(12) United States Patent
Ibanez et al.

(10) Patent No.: US 8,367,002 B2
(45) Date of Patent: Feb. 5, 2013

(54) FLUORESCENT ORGANIC NANOCRYSTALS FOR PRODUCING BIOSENSORS

(75) Inventors: Alain Ibanez, Voiron (FR); Virginie Monnier, Grenoble (FR); Nathalie Sanz, Irvillac (FR); Robert Pansu, Palaiseau (FR)

(73) Assignee: Centre National de la Recherche Scientifique—CNRS, Paris (FR)

( * ) Notice: Subject to any disclaimer, the term of this patent is extended or adjusted under 35 U.S.C. 154(b) by 374 days.

(21) Appl. No.: 12/532,128

(22) PCT Filed: Mar. 21, 2008

(86) PCT No.: PCT/FR2008/050490
§ 371 (c)(1),
(2), (4) Date: Dec. 8, 2009

(87) PCT Pub. No.: WO2008/145875
PCT Pub. Date: Dec. 4, 2008

(65) Prior Publication Data
US 2010/0104476 A1 Apr. 29, 2010

(30) Foreign Application Priority Data
Mar. 21, 2007 (FR) ...................................... 07 53947

(51) Int. Cl.
*G01N 21/64* (2006.01)
(52) U.S. Cl. .................................................. 422/82.08
(58) Field of Classification Search .................... 422/82, 422/82.08
See application file for complete search history.

(56) References Cited

U.S. PATENT DOCUMENTS
6,770,220 B1 8/2004 Klimant

FOREIGN PATENT DOCUMENTS
| EP | 1 541 656 A1 | 6/2005 |
| FR | 2853307 A1 | 4/2003 |
| FR | 2 854 696 | 5/2003 |
| WO | WO 2004/042376 A1 | 5/2004 |
| WO | WO 2007/045755 A1 | 4/2007 |

OTHER PUBLICATIONS

Treussart et al., "Second Harmonic Generation and Fluorescence of CMONS Dye Nanocrystals Grown in a Sol-Gel Thin Film", ChemPhysChem 2003, 4, 757-760.*
He et al., "Synthesis and room temperature photoluminescence of AgI nanoparticles embedded in silica sol-gel coating", Solid State Ionics, 175, 651-654 (2004).*

(Continued)

*Primary Examiner* — Jill Warden
*Assistant Examiner* — Monique Cole
(74) *Attorney, Agent, or Firm* — Arent Fox LLP

(57) ABSTRACT

The present invention relates to a (nano)material comprising at least one inorganic and/or organomineral layer, integrated into which is at least one type of organic or organometallic fluorescent nanocrystal that emerges from the surface of said layer so that at least one part of the fluorescent nanocrystals is in direct contact with the outside environment. These emerging nanocrystals constitute, due to their fluorescence, a signalling function, and they may thus be functionalised by grafting a biomolecule bearing a probe function, such as a half-strand of DNA, to thus produce a biochip, biocaptor or biosensor comprising such a (nano)material, a support for a biochip, biocaptor or biosensor, and a method for preparing such a nanomaterial.

20 Claims, 3 Drawing Sheets

OTHER PUBLICATIONS

Botzung-Appert et al.; "Spatial control of organic nanocrystal nucleation in sol-gel thin films for 3-D optical data storage devices or chemical multi-sensors"; Journal of Crystal Growth; Elsevier; Amsterdam, NL; vol. 283; No. 3-4; Oct. 1, 2005; pp. 444-449; XP005065765.

David Avnir et al.; Organic Fluorescent Dyes Trapped in Silica and Silica-Titania Thin Films by the Sol-Gel Method. Photophysical, Film and Cage Properties; Journal of Non-Crystalline Solids; 1985, 395-406, vol. 74, Elsevier Science Publishers B.V.

Clêment Sanchez et al.; Design of Hybrid Organic-Inorganic Materials Synthesized Via Sol-Gel Chemistry; New Journal of Chemistry; 1994, 1007-1047, vol. 18, No. 10.

David L. Gerhold et al.; Better Therapeutics Through Microarrays; Nature Genetics Supplement; Dec. 2002, 547-552, vol. 32.

Margaret A. Shipp et al.; Diffuse large B-Cell Lymphoma Outcome Prediction by Gene-expression Profiling and Supervised Machine Learning; Nature Medicine; Jan. 2002, 68-74, vol. 8, No. 1.

Luis Quijada et al.; Genomic DNA Macroarrays as a Tool for Analysis of Gene Expression in *Leishmania*; Experimental Parasitology; 2005, 64-70, vo. 111, Elsevier Inc.

Arindam Bhattacharjee et al.; Classification of Human Lung Carcinomas by mRNA Expression Profiling Reveals Distinct Adenocarcinoma Subclasses; PNAS; Nov. 20, 2001, 13790-13795, vol. 98, No. 24.

Howard Y. Chang et al.; Robustness, scalability, and integration of a Wound-Response Gene Expression Signature in Predicting Breast Cancer Survival; PNSA; Mar. 8, 2005, 3738-3743, vol. 102, No. 10.

B. Foultier et al.; Comparison of DNA Detection Methods Using Nanoparticles and Silver Enhancement; IEE Proceedings-Nanobiotechnology; Feb. 2005; 3-12, vol. 152, No. 1.

Philipp Angenedt; Progress in Protein and Antibody Microarray Technology; Drug Discovery Today; Apr. 2005; 503-511, vol. 10, No. 7.

V. Monnier et al, "Confined nucleation and growth of organic nanocrystals in sol-gel matrices", J. Mater. Chem., 2006, 16, 1401-1409.

E. Botzung-Appert et al, "Polyaromatic luminescent nanocrystals for chemical and biological sensors", Chem. Mater, 16, 2004, 1609-1611.

A. Ibanez et al, "Controlled nanocrystallization of organic molecules in sol-gel glasses", Adv. Mater., 10, 1998, 1540-1543.

N. Sanz et al, "Organic nanocrystals grown in sol-gel coating", J. Mater. Chem., 10, 2000, 2723-2726.

F. Treussart et al, "Second Harmonic Generation and Fluorescence of CMONS Dye Nanocrystals Grown in a Sol-Gel Thin Film", Chem. Phys. Chem., 2003, 4, 757-760.

\* cited by examiner

FLUORESCENT ORGANIC NANOCRYSTALS FOR PRODUCING BIOSENSORS

CROSS-REFERENCE TO RELATED APPLICATION

This application is a National Stage entry of International Application No. PCT/FR2008/050490, filed Mar. 21, 2008, which claims priority to French Application Number 07/53947, filed Mar. 21, 2007, the disclosure of the prior applications is hereby incorporated in their entirety by reference.

TECHNICAL FIELD

The present invention relates to the field of materials having optical properties, and more particularly captors and sensors, in particularly biological ones. More particularly, these can be chips, more particularly biochips, and more particularly fluorescent biochips.

In the description hereinunder, the references between square brackets ([ ]) refer to the list of references given after the examples.

STATE OF THE ART

Biochips are major tools in clinical research and more particularly as regards the development of diagnostic and prognostic tests as well as in the research for new therapeutic procedures.

The most currently used biochips are fluorescent biochips. However, these can have an insufficient sensitivity to carry out the analysis of precious and expensive, fragile and/or complicated to manufacture samples. Biochips can also be insufficiently transparent, more particularly in some wavelengths such as the infra-red. They also can be insufficiently stable and for example not have a satisfactory chemical or temporal resistance.

More particularly, the methods making it possible to prepare the materials for producing chips, and more particularly biochips or to prepare the chips are generally expensive, difficult to produce on an "industrial scale" (more particularly for preparing a large number of chips at the same time and/or in one operation), delicate and/or complex to implement.

There so exists a need for chips which make it possible to solve as a whole or in part the above mentioned problems, more particularly as regards thermal, mechanical, chemical and/or photochemical resistance; and/or biochips which make it possible to have good optical properties such as fluorescence, a good stability, a large range of transparency as well as a method for easy manufacturing and shaping and a low diffusion and a good stability.

On the other hand, there also exists a need for a (nano) material making it possible to prepare chips allowing to solve as a whole or a part the above-mentioned problems.

There exists a need for a method for preparing this (nano) material allowing to solve as a whole or in part the above mentioned problems.

DESCRIPTION OF THE INVENTION

Thus, according to a first aspect, the object of the invention is a (nano)material comprising at least one inorganic and/or organomineral layer, wherein is integrated at least one type of luminescent nanocrystal at least one part of which is in direct contact with the outside environment.

Advantageously, the luminescent organic or organometallic nanocrystals are fluorescent nanocrystals.

In one embodiment, the (nano)material comprises at least one inorganic and/or organomineral layer, wherein is integrated at least one type of organic or organometallic fluorescent nanocrystal that emerges from the surface of said layer so that at least one part of the nanocrystal is in direct contact with the outside environment.

"(Nano)material" means, in the sense of the present invention, a material or a nanomaterial such as defined hereinunder.

"Nanomaterial" means, in the sense of the present invention, a material having nanometric dimensions, i.e. a material at least one of the dimensions of which is at a nanometric scale. In other words, it is a material having nanometric dimensions in at least one of the dimensions of space. For example, the size of the material in at least one of the dimensions of space is comprised between 1 and 500 nm, preferably between 1 and 100 nm. For example, it can be a thin layer.

"Organomineral layer" means, in the sense of the present invention, an array comprising at least one mineral compound and at least one organic compound. Thus, the organomineral layer may be a sol-gel layer, for example of the Silicate, Titanate, Zirconate, Stannate, Borate, Aluminate or Yttriate types and comprising at least organic or organometallic nanocrystals.

The sol-gel layer may more particularly be mainly composed of amorphous silicate/silicon oxide which may result from the hydrolysis and polycondensation of silicon alkoxides comprised in the initial solution. However, the sol-gel layer or the polymeric network may also contain alkyl, aryl and/or aralkyl carbon radicals.

The inorganic and/or organomineral layer may also more particularly comprise one layer of sol-gel.

This sol-gel layer may more particularly be one of the silicate or metallic types, more particularly accessible from silicon alcoxide, titanium alcoxide or other metal precursors, more particularly selected among Titanium, Zirconium, Tin, Boron, Aluminium and Yttrium.

According to the purpose of the array (hydrophylic-hydrophobic balance, improvement of crystallinity, size of nanocrystals, . . . ), the various types of alcoxide may be used to 100% or as a mixture with variable proportions.

The sol-gel chemistry and the various embodiments thereof are known to the person skilled in the art and have been the subject of numerous reports and publications and thus will not be developed within the scope of this patent. For example, we shall mention the work by C. J. Brinker and G. W. Scherer, Sol-gel Science, The Physics and Chemistry of SolGel Processing, Academic Press, New York, 1990 [ref 1]. Other synthesis articles can also be mentioned such as D. Avnir, V. R. Kaufman and R. Reisfeld, J. Non. Cryst. Solids, 1985, 74, 395-406 [ref 2]; and C. Sanchez and F. Ribot, New J. Chem., 1994, 18, 1007-1047 [ref 3].

Generally speaking, the inorganic and/or organomineral layer comprising a sol-gel layer may be obtained from a sol-gel mixture. Advantageously, the sol-gel mixture contains at least one fluorescent organic or organometallic compound. Advantageously, this fluorescent organic or organometallic compound initially dissolved in the sol-gel mixture is crystallised within the sol-gel array to form fluorescent organic or organometallic nanocrystals. The crystallisation may be carried out by drying the sol-gel mixture containing the organic or organometallic fluorescent compound. The drying speed can be adjusted to favour the formation of nanocrystals.

"Sol-gel" mixture means, in the sense of the present invention, a mixture initially comprising at least one metallic alcoxide in presence of water, at least one organic solvent and at least one fluorescent organic or organometallic compound, with said mixture being initially in the form of a solution and producing a gel because of a hydrolysis and polycondensation reaction. As a matter of fact, the presence of water allows to initiate hydrolysis and condensation reactions of the metallic alcoxides forming an inorganic network leading to gels and then xerogels. Such xerogels lead to a structured inorganic solid network of metallic oxides. The sol-gel chemistry is for example mentioned in the French patent FR 2 853 307 [ref 4].

The sol-gel layer may to be obtained from any metallic alcoxide known to the person skilled in the art and compatible with the sol-gel chemistry.

Then in one embodiment, the sol-gel layer may be obtained from a metallic alcoxide having the following formula (I):

wherein:
M is a metal selected from the group comprising Si, Ti Zr, Sn, B, Al and Y, for example Si.
x is a integer from 0 to 2, for example 0 or 1;
y is an integer from 1 to 6, for example 3 or 4;
x+y corresponds to the coordination number of the metal M;
$R^1$ and $R^2$ each independently represent an organic radical compatible with the sol-gel chemistry.

The man skilled in the art will know how to select $R^1$ and $R^2$ when reading the above-mentioned works and his general knowledge in the field of sol-gel chemistry. The examples given hereinunder are given only for an illustration and are not limitative in any way.

For example, $R^1$ and $R^2$ may independently represent an alkyl, aryl or aralkyl carbon radical.

The alkyl radicals may be linear or branched, cyclic or acyclic, saturated or unsaturated and they also may comprise or bear heteroatoms more particularly O, N, S, B and P. For example, it may be $C_{1-15}$alkyle; $C_{2-15}$alcenyl; $C_{2-15}$alcynyl; $C_{3-15}$cycloalkyl.

The alkyl radicals may comprise or bear from 1 to 15 atoms of carbon and more particularly be selected among the methyl, ethyl, propyl, butyl, pentyl, hexyl, heptyl, octyl, nonyl, decyl, undecyl and dodecyl radicals. According to the invention, the alkyl radical comprises 1 to 15 atoms of carbon, for example 1 to 10 atoms of carbon, for example 1 to 6 atoms of carbon.

It should be noted that the alkyl radicals may also comprise or bear one or several heteroatoms, more particularly selected in the group comprising oxygen, sulphur, nitrogen, phosphor and boron. In other words, the compounds of formula (I) in which $R^1$ and/or $R^2$ is an alkyl radical comprise the compounds having the formula (I) in which $R^1$ and/or $R^2$ is an heteroalkyl radical. This may for example be a heteroalkyl, a heteroalkenyl, a heteroalcynyl, a heterocycle, an alkoxy, an alkylthio, an alkylamine, an alkylamide, an alkylimine, an alkylimide, an alkylesther, an alkyether, etc. According to the invention, the heteroalkyl radical may comprise 1 to 15 atoms of carbon, for example 1 to 10 atoms of carbon, for example 1 to 6 atoms of carbon.

"Aryl" means, in the sense of the present invention, a radical comprising at least a cycle meeting the Hückel aromaticity rule. Said aryl may be mono- or polycyclic, merged or not. The aryl radicals may comprise from 4 to 15 atoms of carbon, more particularly from 6 to 10 atoms of carbon and possibly comprise heteroatoms more particularly O, N, S. Among the aryl radicals, phenyl, naphtyl and pyridinyl radicals can be mentioned.

It should be noted that the aryl radicals may comprise or bear one or several heteroatoms, more particularly selected from the group comprising oxygen, sulphur, nitrogen and phosphor. In other words, the compounds having the formula (I) where $R^1$ and/or $R^2$ and an aryl radical comprise the formula (I) compound where $R^1$ and/or $R^2$ is an heteroaryl radical, i.e. a cyclic or polycyclic aromatic hydrocarbon group, wherein at least one atom of carbon is substituted for an heteroatom more particularly selected from the group comprising oxygen, sulphur and nitrogen.

"Aralkyl" means, in the sense of the present invention, an alkyl radical substituted by an aryl radical, with the terms "alkyl" and "aryl" being such as defined hereabove. The point where the "aralkyl" radical is connected to the rest of the molecule (i.e. the metal M in the formula (I)) is at the level of the alkyl group. The aralkyl radicals may comprise 4 to 30 atoms of carbon, more particularly from 6 to 20 atoms of carbon and may comprise or be substituted by alkyl radicals and/or heteroatoms, more particularly O, N, S and P. Among the aralkyl radicals, it may be benzyl and tolyl.

In one particular embodiment, $R^1$ and $R^2$ may independently represent a $C_1$ to $C_{15}$ alkyl radical, $C_1$ to $C_{15}$ heteroalkyl, $C_6$ to $C_{25}$ aryl, $C_4$ to $C_{25}$ heteroaryl, or $C_6$ to $C_{20}$ aralkyl; the radicals $R^1$ and $R^2$ being potentially independently substituted by one or several groups R independently selected from the group comprising a $C_1$ to $C_{10}$ alkyl radical, $C_1$ to $C_{10}$ heteroalkyl; $C_6$ to $C_{10}$ aryl or $C_4$ to $C_{10}$ heteroaryl; F; Cl; Br; I; —$NO_2$; —CN; or a function -$GR^{G1}$ wherein G is —O—, —S—, —$NR^{G2}$—, —C(=O)-, —C(=O)O-, —C(=O)$NR^{G2}$—, where each occurrence of $R^{G1}$, $R^{G2}$ and $R^{G3}$ is independently from the other occurrences of $R^{G1}$ an atom of hydrogen or a $C_1$ to $C_{10}$ alkyl radical, $C_1$ to $C_{10}$ heteroalkyl; $C_6$ to $C_{10}$ aryl or $C_4$ to $C_{10}$ heteroaryl; or when G represents —$NR^{G2}$—, $R^{G1}$ and $R^{G2}$ together with the atom of nitrogen which they are bound to, form an heterocycle or the possibly substituted heteroaryl.

The alkyl, aryl and/or aralkyl radicals may be bound directly to the silicon, titanium, zirconium, tin, boron, aluminium, yttrium atoms more particularly by a covalent bond. Then, we can call them hydrid organomineral materials, as well as for example known materials in the field of contact lens obtained by sol-gel.

The sol-gel layer may comprise only silicon, or silicon and titanium, zirconium and/or tin. This sol-gel layer may more particularly be obtained by using other types of metallic alkoxides such as titanium, zirconium and/or tin alkoxides.

As soon as the sol-gel mixture is made, the metallic alcoxides react by hydrolysis and condensation reactions which lead to "inorganic polymers". In the field of sol-gel chemistry, the term "inorganic polymer" is used by analogy with the organic polymers. For an illustrative purpose, the following reactions of hydrolysis (1) and condensation (2) of metallic alcoxide can occur.

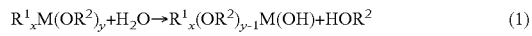

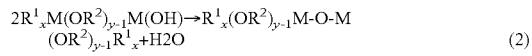

where $R^1$, $R^2$, x and y are such as previously defined.

Advantageously, the sol-gel mixture of the method of the invention may be homogeneous and chemically and mechanically stable. For example, it may be stable for several months or even several years which is a great advantage for the practical implementation of the present invention.

"Metallic alcoxides", also called "sol-gel precursors" means, in the sense of the present invention, any metallic compound having the formula (I). According to the invention, any metallic alcoxide known to the man skilled in the art may be used in so far as an interconnected polymeric sol-gel network can be obtained. The man skilled in the art will more particularly be able to use any known metallic alcoxide belonging to the sol-gel chemistry. Therefore, the reader can more particularly refer to the reference book by C. J. Brinker and G. W. Scherer, Sol-Gel Science, The Physics and Chemistry of SolGel Processing, Academic Press, New York, 1990 [ref 1]. Also refer to ref 2 and 3.

"Solvent", in the sense of the present invention, means any solvent known to the man skilled in the art and compatible with the method for implementing the present invention, i.e. which can make metallic alcoxides and hydrolysis water miscible so as to obtain homogeneous solutions, more particularly with a view to their shaping in thin layers or as films. Advantageously, the solvent makes it possible to completely dissolve the fluorescent compound.

The solvent may for example be selected from the group comprising $R^S$—OH alcohols where $R^S$ is a $C_1$ to $C_6$ alkyl radical, $R^{S1}$—C(=O)—$R^{S2}$ ketons, $R^{S1}$—O—$R^{S2}$ ethers, where $R^{S1}$ and $R^{S2}$ are independently $C_1$ to $C_6$ alkyl radicals, tetrahydrofurane, acetonitril, dimethylformamide, toluene, dimethylsulfoxide, dioxiane, acetone, acetic acid, formic acid, dichloromethane, chloroform, dichloroethane, ethyl acetate, diethylether or a mixture thereof.

According to the invention, water present in the sol-gel mixture may be initially introduced in a small quantity, with the latter being sufficient for initiating the reactions leading to the polycondensation of the inorganic network or in a quantity greater than the initial quantity of metallic alcoxide. For example, the sol-gel mixture can initially comprise a molar percentage of water with respect to the number of alcoxide functions (—$OR^2$) from 10 to 400%, preferably from 20 to 100% and more preferably from 50 to 100%.

Silicate precursors silicon alcoxides can be chosen for example from the group comprising tetramethoxisilane (TMOS, $Si(OCH_3)_4$), tetraethoxisilane (TEOS, $Si(OC_2H_5)_4$) methyltrimethoxisilane (MTMOS, $CH_3Si(OCH_3)_3$), methyltriethoxisilane (MTEOS, $CH_3Si(OC_2H_5)_3$), ethyltriethoxisilane (ETEOS, $C_2H_5Si(OC_2H_5)_3$), 1,2-bis(trimethoxisilyl) ethane (TMSE), 3-glycidoxipropyl)trimethoxisilane (GPTMS) or a mixture thereof.

For metallic alcoxide precursors of titanates, zirconates, stannates, borate, aluminates and yttriates the reader can refer for example to C. J. Brinker and G. W. Scherer, Sol-Gel Science, The Physics and Chemistry of SolGel Processing, Academic Press, New York, 1990 [ref 1]. And also refer to ref 2 and 3.

In the case of an array obtained by mixing an equimolar mixture of MTMOS and TMOS, the non-linking methyl substituents of MTMOS can at least partly cover the gel pores and favour the aggregation of nanocrystals, whereas the silanol groups can form bonds and more particularly hydrogen bonds with the organic molecules.

More particularly, the inorganic and/or organomineral layer, more particularly the sol-gel layer, is in the form of a film.

"Film" means, in the sense of the present invention, a structure wherein the thickness is of the order of a few hundred nanometres or of the order of the micrometre, and more particularly a thickness from 50 nm to 1,500 nm and more particularly from 80 to 1,200 nm, or even 100 to 1,000 nm.

More particularly, this film has a width and/or a length of 1 mm to 10 cm, more particularly between 5 mm and 5 cm.

Nanocrystals may be fluorescent, and more particularly absorb and re-emit light in the wavelengths of the visible or close to the infra-red.

Luminescence can spread on a set of luminescent molecules or chromophores, for example from $10^3$ to $10^{10}$, more particularly $10^3$ to $10^9$, more particularly $10^4$ to $10^8$, or even $10^5$ to $10^7$ molecules per nanocrystal.

More particularly, nanocrystals emit a fluorescence which is spread on all the fluorophores and which is put out or "quenched" simultaneously. "Simultaneously" means from 0.001 to 10 ns, more particularly 0.01 to 5 ns, even more particularly from 0.1 to 2 ns, or even from 0.5 to 1.5 ns.

"Fluorescent" compound or nanocrystal means, in the sense of the present invention, a compound or a nanocrystal having the property of emitting further to a light excitation, an electromagnetic radiation in the field of the visible light or in the close infra-red light (IR). The excitation light signal may come from a light source such as a laser, an arc lamp or electroluminescent diodes (LED). For example, the fluorescent compound or nanocrystal may emit an electromagnetic radiation at the wavelengths of 400 to 1,200 nm which correspond to the window of relative transparency of living tissues. For example, the fluorescent compound or nanocrystal may emit an electromagnetic radiation at the wavelengths of 400 to 1000 nm, for example 550 to 800 nm which correspond to fluorescence in the red and close infra-red. More particularly, the fluorescent compound or nanocrystal may emit fluorescence in the visible and close infra-red. Nanocrystals may be organic or organometallic nanocrystals, more particularly be fluorescent and more particularly comprise at least one, or even be constituted of one fluorescent compound in a crystalline state.

Nanocrystals may comprise at least an organic molecule compound or coordination composite which fluoresces in this solid state and is soluble in an organic solvent.

According to the invention, the organic or fluorescent organometallic compound may be for example selected from the group comprising fluorescent compounds of the polyaromatic series, for example diphenylanthracene, rubrene or tetracene, aromatic series, for example 4-(N,N-diethylamino)-b-nitrostyrene (DEANST), 1,4-di(2,5-phenyloxazole) benzene (POPOP) or N-4-nitrophenyl-(L)-prolinol (NPP), the stilbene (CMONS), diethyl-amino-nitro-stilbene- or the stilbene, the naphtilimid series for example naphtilimide, the rhodamine series for example rhodamine B, auramine series for example auramine O, diimide perylene series, dipyrromethene-boron difluoride derivatives, rare earth composites for example europium composites.

The fluorescent compound in the solid state or even in the crystalline state may more particularly be selected from a group comprising cyanomethoxynitrostilbene, naphtilimide, polyaromatic molecules such as rubrene or tetracene, diimide perylene, diphenylanthracene, derivatives of dipyrromethene boron difluoride (Bodipy®) and europium composites.

In a particular embodiment, the fluorescent compound is selected from the polyaromatic series such as rubrene, auramine O or rhodamine B for example.

Nanocrystal may be inserted into the pores of the inorganic and/or organomineral layer.

"Pores" means, in the sense of the present invention, gaps or voids between the links of the network forming the inorganic and/or organomineral layer (for example the silicate, titanate, zirconate, stannate, borate, aluminate, yttirate etc. network) which has polymerised/polycondensed during the sol-gel method.

The nanocrystals observed by transmission electron microscopy may have a spherical shape and may have a diameter from 10 to 500 nm, more particularly from 100 to 400 nm, more particularly from 150 to 300 nm.

Nanocrystals may have a rather homogeneous size distribution, more particularly varying in maximum +/−20%, or even +/−10%.

The nanocrystals present in the inorganic and/or organomineral layer have at least one part in direct contact with the outside environment, more particularly they emerge by approximately 2 to 50% of their diameter with respect to the inorganic and/or organomineral layer, or even from 5 to 30% of the diameter, more particularly when the nanocrystals are spherical. The inorganic and/or organomineral layer may be a sol-gel array.

The nanocrystals can emerge from the inorganic and/or organomineral layer by 1 to 100 nm, more particularly to 2 to 80 nm, or even 3 to 50 nm.

It is sufficient that the nanocrystals slightly emerge from the surface to be in direct contact with the outside (organic solution) either by a few nm to a few tens of nm.

In order to present an optimal resistance, it may be desirable not to pickle too much the surface of the sol-gel layers so that the nanocrystals do not emerge too much, to enable an excellent mechanical stabilisation and thus avoid their too easy separation from the sol-gel layer. Thus, the height of the emergence can partly depend on the diameter of the nanocrystals.

Then, according to a particular embodiment, the height of the emergence does not exceed one third of the diameter of the nanocrystals, more particularly so that they remain anchored in the sol-gel layer.

This measure may more particularly be carried out by an atomic force microscopy in an intermittent oscillating mode by recording the topography of the sample.

Advantageously, the nanocrystals present in the inorganic and/or organomineral layer are rigidly anchored therein, more particularly they can resist an immersion in an biologic solution to be analysed (DNA strands, proteins . . . ) and this during a few minutes.

"Resisting" means that more than 95%, more precisely more than 99%, or even more than 99.9% of the nanocrystals present at the beginning of the test are still present in the (nano)material at the end of the test.

In a particular embodiment, such nanocrystals may have at least one type of probe on their surface. The nanocrystals may have one or several identical or different types of probes, for example one, two, three, four or five identical or different probes and more particularly one, two, three, four or five probes of different types.

At least one probe may thus be chosen from the group comprising the coloured indicators, the DNA, the oligonucleotides or the polynucleotides, the polypeptides, the proteins, the antibodies, the carbohydrates, the glycoproteins and the lipids. For example, the coloured indicators can be selected among the pH, redox and/or complexation indicators.

This probe may be simply absorbed or grafted on the nanocrystals, more particularly via a chemical bond. For example, the probe can be absorbed or grafted more particularly via a covalent, ionic, electrostatic, ionocovalent bond, a hydrogen bond, hydrophobic interactions or van der waals forces.

The probe may be chemically modified with an appropriate chemical function so as to able to be grafted on the surface of the nanocrystal.

Advantageously, the possibly chemically modified probe does not bind to the surface of the sol-gel layer, more particularly it is insensitive to the M-OH free sites present at the surface of the sol-gel layer.

Then, as the nanocrystals that emerge constitute, thanks to their fluorescence, the signalling function may also be functionalised by grafting a biomolecule bearing a probe function, such as a half-strand of DNA, thus to produce a biochip, sensor or captor, comprising a (nano)material according to the invention or a support for a biochip, captor or sensor. This aspect of the invention is more particularly discussed in the following sections.

According to another aspect, the invention aims at a method for manufacturing a (nano)material according to the invention, more particularly comprising an inorganic and/or organic-mineral layer, wherein is integrated at least one type of organic or organometallic fluorescent nanocrystal that emerges from the surface of said layer so that at least one part is in direct contact with the outside environment comprising at least the following step:

a) dissolution of a part of an inorganic and/or organomineral layer so as to make at least a part of the nanocrystals of the inorganic and/or organomineral layer emerge or increase the surface of the nanocrystals in contact with the outside environment. More particularly, in the step of dissolution, said inorganic and/or organomineral layer comprises or includes at least one type of fluorescent nanocrystal.

This step of partial dissolution of the sol-gel layer can be carried out by agents, more particularly chemical agents, allowing to homogenously pickle the surface of the inorganic and/or organomineral layer, more particularly without damaging the fluorescence property of the nanocrystals.

More particularly, this step is carried out by agents allowing to pickle, which are selected among basic aqueous solutions, more particularly inorganic or organic bases, strong or weak bases, more particularly soda, ammonia and/or potash bases. More particularly, these basic solutions have a basic concentration from $10^{-6}$ to $10^{-1}$ M, and more particularly from $10^{-3}$ to $10^{-1}$ M.

Thus, this step may enable a regular thinning of the inorganic and/or organomineral layer by pickling the surface of the inorganic and/or organomineral layer, and in particular silicated sol-gel arrays.

More particularly, this step of controlled dissolution enables a thinning speed from 5 to 100 nm/hr, or even 10 to 50 nm/hr.

The method according to the invention may also comprise a step consisting in preparing at least one array layer, more particularly sol-gel array layer comprising or including nanocrystals.

Thus, in a particular embodiment, the invention relates to a method for producing (nano)material comprising an inorganic and/or organomineral layer in which is integrated at least one type of organic or organometallic fluorescent nanocrystal that emerges from the surface of said layer so that at least a part thereof is in direct contact with the outside environment, said method comprising:

a) a step consisting in preparing at least an inorganic and/or organomineral layer comprising or including organic or organometallic fluorescent nanocrystals, and b) a step of dissolution of a part of said inorganic and/or organomineral layer obtained in step a) so as to make at least a part of the nanocrystals of the inorganic and/or organomineral layer emerge or to increase the surface of the nanocrystals in contact with the outside environment.

In one embodiment, the inorganic and/or organomineral layer is a sol-gel layer. Thus, for the step a) may comprise a prior step (0) of preparing a sol-gel mixture comprising:

(i) a step (0a) of preparation of an initial sol-gel mixture, for example by mixing in a solvent at least one organic or organometallic fluorescent compound and at least one metallic alcoxide, for example having a formula (I) in the presence of water; and possibly, (ii) a step of storage (0b) of the initial sol-gel mixture for a time d, so as to let the initial mixture react.

According to the invention, the time d may be less than several months or even several years. For example, the time d may be 1 day to 1 year, for example 7 days to 21 days. As a matter of fact, the storage of the mixture allows to let the mixture age, so as to advance the reaction of hydrolysis and condensation of metallic alcoxides.

According to the invention, the step (0) of preparation of the sol-gel mixture may comprise the addition of an acid to the initial mixture. As a matter of fact, while it lowers the pH of the mixture, the acid allows to favour the obtaining of long inorganic chains which are favourable to the formation of an inorganic and/or organomineral layer around the organic or organometallic crystals. According to the invention, the pH the mixture can be from 1 to 7, more preferably from 1 to 2.

"Acid" means, in the sense of the present invention, Brönsted acids, whether mineral or organic. Among the acids which can be used, for example hydrochloric acid, nitric acid or acetic acid can be mentioned.

The organic or organometallic fluorescent compound, the metallic alcoxide and the solvent may be selected according to any one of the above-mentioned embodiments for implementing the nanomaterials of the invention.

The step a) may more particularly be carried out by the crystallisation of fluorescent organic or organometallic nanocrystals in thin layers of the sol-gel array. More particularly, this step may be carried out by spin-coating.

More particularly, the construction of this inorganic and/or organomineral layer, possibly in the form of a thin layer, may be carried out at room temperature through the hydrolysis and condensation of a solution comprising precursors of the inorganic and/or organomineral layer, more particularly sol-gel layer such as silicon alcoxides wherein the organic or organometallic molecules are dissolved in a solvent, more particularly in an organic one.

"Organo-metallic" means compounds comprising an organic part and a metallic part.

Nanocrystallisation may result from a strong instantaneous nucleation followed by the control of the growth of nuclei through the viscosity and/or porosity of the gel. Oversaturation of the organic phase may be caused by the very quick evaporation of the organic solvent.

More particularly, in the spin-coating procedure according to the rotation speed which can for example be 1,000 to 4,000 rpm, the viscosity of the solvent or the deposition time of the thin and/or transparent layers, for example 100 to 1,000 nm may be carried out.

The inorganic and/or organomineral layer of the step a) may then be submitted to an annealing step, more particularly at temperatures close to the melting point of the organic nanocrystals. This annealing step is intended to eliminate any trace of solvent and to further stabilise the sol-gel layer, more particularly inorganic one (elimination of residual solvent, densification of the array). The annealing step may be carried out more particularly at temperatures from 50 to 250° C., more particularly from 80 to 150° C.

"Temperature close to the melting point" means, in the sense of the present invention, a temperature within a range from the melting point minus 5° C. to the melting point minus 100° C., more particularly the melting point minus 10° C. to the melting point minus 50° C.

This annealing step may also comprise the improvement of the crystallinity of aggregates and/or the stabilisation of the inorganic and/or organomineral layer.

The size of the nanocrystals may thus be adjusted according to the conditions of the confined nanocrystallisation in the inorganic and/or organomineral layer, more particularly in the sol-gel array, more particularly the silicated array.

As nanocrystals are fluorescent, they may be viewed using techniques such as confocal photonic microscopy. This is illustrated in FIG. 2 which is a confocal photonic microscopic picture of rubrene nanocrystals in a sol-gel array.

In the case where nanocrystals have a size smaller than 100 nm, the transmission electron microscopy may be used to observe the distribution and the size of nanocrystals. This is illustrated in FIG. 3 which is a transmission electronic microscopic image of rubrene nanocrystals in the sol-gel array.

Such direct viewings of nanocrystals make it possible to adjust the parameters having an effect on the confined crystallisation of chromophores (organic or organometallic fluorescent molecules), more particularly on the nature of the precursors making it possible to form the sol-gel array, for example the nature of silicon alcoxide, hydrolysis kinetics and condensation, the nature and the rate of solvent, the concentration in fluorophores, the oversaturation and the centrifugation parameters.

According to another object, the present invention relates to a (nano)material film according to the invention. In a particular embodiment, it relates to a film comprising a sol-gel array comprising mechanically stabilised nanocrystals, said nanocrystals that emerge from the surface of said film, so that at least a part of each nanocrystal is in direct contact with the outside environment. More particularly, the (nano)material is a sol-gel array comprising mechanically stabilised nanocrystals, said nanocrystals that emerge from the surface of said film so that at least a part of each nanocrystal is in direct contact with the outside environment, positioned on a solid support of the glass slide, for example.

The techniques for the preparation of such films are known to the man skilled in the art and will not be developed in the present application. In this context, several sol-gel thin layers deposition methods may be used: the substrate centrifugation techniques (several thousands of rotations per minute). Other techniques such as the dip-coating can be also used. The reader can refer to the work by Brinker and Scherer mentioned above [Ref 1].

As mentioned hereabove, the devices based on the detection of a fluorescent signal are more particularly used in the field based on the detection of chemical or biological reactions (for example biochips).

Biochips are a biochemical tool for the massive collection of information, more particularly on nucleic acids (DNA chips) and amino acids (protein chips), antigens and antibodies (immunologic captors). Associated to the digital processing techniques of the collected information, the DNA chips make it possible to lead researches (detection, separation, identification, study) allowing to have a direct access to DNA.

Protein chips make it possible to detect, identify, separate, study proteins and determine the activities, functions, interactions, modifications thereof over time.

Immunologic captors based on a bond with an enzyme make it possible to detect antibodies/antigens.

Generally speaking, a field of application of the invention more particularly relates to the chips, more particularly biochips, captors and sensors which are in the form of a solid support at the surface of which biochemical elements are immobilised.

Thus, the present invention may more particularly be applied in the production of supports for biochips, biocaptors or biosensors. It more particularly relates to biochips supports compatible with the grafting of nucleic acids (DNA biochips, ARN biochips), amino acids (protein chips, immunologic chips), as well as cellular biochips used more particularly in transfection studies.

Thus and according to one of its aspects, the invention relates to a support for a biochip, captor or sensor comprising a substrate the surface of which comprises a layer of the (nano)material or film according to the invention. In one embodiment, the (nano)material comprises at least an inorganic layer and/or organomineral layer wherein is integrated at least a type of organic or organometallic fluorescent nanocrystal that emerges from the surface of said layer, so that at least a part of the nanocrystal is in direct contact with the outside environment.

In one embodiment, the support comprises a substrate on which the (nano)material of the present invention is deposited, more particularly as a thin layer or a film. It may be any solid material known to the man skilled in the art, such as for example support materials used for the production of analysis microsystems and biochips. It may also be an organic or inorganic substrate. It may be made for example of a material selected from the group comprising glass, silicon, polycarbonate, nymon, polymethylmethacrylate (PMMA), polystyrene, cycloolefin copolymer (COC) and acrylonitrile polystyrene (SAN). The support is typically a glass slide which can be compared to microscope slide.

The substrate may be cleaned beforehand so that the adherence of the (nano)material layer to the surface thereof is improved. Such cleaning may for example be a chemical cleaning, possibly followed by a thermal treatment. Cleaning techniques, more particularly those used for the preparation of supports for biochips, captors and sensors, known to the man skilled in the art may be used. For this cleaning, any appropriate solvent may be used for dedusting and/or degreasing the surface of the substrate, preferably without damaging it. For example, trichloroethylene, acetone, ethylic alcohol, deionised water, acid or basic solutions, etc. can be mentioned as a cleaning solvent. Cleaning may consist in soaking the substrate in one or several of these solvents successively. Cleaning is then generally followed by drying. Cleaning can also consist simply in removing dust from the substrate using a compressed air jet.

The (nano)material layer may be deposited onto the surface of the substrate using any technique known to the man skilled in the art for depositing such type of material onto the surface. More particularly, when the (nano)material comprises a sol-gel layer, this step can be carried out as follows:
(i) a step (0a) of preparation of the initial mixture, for example by mixing in a solvent at least one organic or organometallic fluorescent compound and at least one metallic alcoxide, for example having the formula (I) in the presence of water; possibly,
(ii) a step of storing (0b) the initial mixture for a time d so as to let the initial mixture react, and
(iii) a step of depositing the sol-gel mixture obtained during step (ii) onto the support, and
(iv) a step of spin-coating to obtain an inorganic and/or organomineral layer comprising organic or organometallic fluorescent nanocrystals at the surface of the support.

As a matter of fact, as the sol-gel mixture is prepared by hydrolysis and condensation of salt or metal alcoxides or metalloids M, advantageously in the presence of an organic solvent, this organic solvent may facilitate the deposition and the drying of the layer of the (nano)material onto the substrate.

In one embodiment, the (nano)material layer according to the invention may be deposited onto said surface of the substrate to a thickness from 50 nm to 1,000 nm, or even 100 nm to 1,000 nm. As a matter of fact, it will be easily understood that the minimum thickness is a thickness advantageously enabling to cover the surface of the substrate without leaving holes. As to the maximum thickness, it is generally preferred not to exceed the micrometre. As a matter of fact, if the thickness is greater than one micrometre, cracking or chipping problems connected to the evaporation of the solvent may occur on the layer (internal tensions resulting from capillary forces; refer to the reference book by Brinker and Scherer [ref 1]). However, it is not necessary to use too important quantities of (nano)material to implement the present invention.

When the inorganic and/or organomineral layer comprising organic or organometallic fluorescent nanocrystals is deposited onto the support, the latter can further be submitted to a step of dissolution of a part of an inorganic and/or organomineral layer so as to make at least a part of the nanocrystals of the inorganic and/or organomineral layer emerge or to increase the surface of the nanocrystals in contact with the outside environment.

The various embodiments described above for the preparation of the (nano)material according to the invention may be applied to the implementation of supports for chips, captors or sensors (e.g. solvents, fluorescent compounds, metallic alcoxides, etc.).

In particular, one or several types of identical or different probes may be grafted or adsorbed on the part of the nanocrystals that emerges from the inorganic and/or organomineral layer. For this purpose, the various embodiment described previously may be applied to the (nano)material of the invention (i.e. probe types, connection modes, etc.).

In a particular embodiment, the support according to the invention may comprise a stack of thin dielectric layers forming a Bragg mirror interposed between the substrate and the layer of nanomaterial. As regards the implementation of this aspect of the invention, the reader may refer to the Genewave Company's patents, for example WO 2004/042376 [Ref 5] and WO 2007/045755 [Ref 6]. These are substrate having a Bragg mirror as a network surface so that the fluorescent signal is totally reflected to the detector in order to increase the sensibility of the system. These substrates are currently called "amplislides".

This particular configuration may make it possible to increase the exciting field inside the layer of the nanomaterial. Thus, this configuration results in the increase of the excitation of the inorganic and/or organometallic luminescent nanocrystals anchored in the layer of the nanomaterial and so the increase of the quantity of light emitted in the substrate. It should be noted that the Bragg mirror is a successive stacking of several thin dielectric layers having different refraction effects $n_1$ and $n_2$. The thickness of each of these layers is equal to $\lambda/(4n)$, with n having the value $n_1$ or $n_2$. The variable l corresponds to the wavelength to which a maximum reflexion is desired for a Bragg mirror. According to another aspect, the invention relates to the utilisation of the (nano)material according to the invention for the production of supports for chips, more particularly supports for biochips, captors or sensors.

According to another aspect, the invention relates to a chip, more particularly a biochip, a captor or a sensor comprising at least one (nano)material or a film according to the invention. The chips more particularly the biochips, captors and sensors and their various operational implementation are known to the persons skilled in the art and are the subject of various reports and publications. As an illustration, reference can be made to (i) D. L. Gerhold, "Better Therapeutics through microarrays", Nature Genetics, 32, p 547-552 (2002) [Ref 7];

(ii) M. A. Shipp "Diffuse large B-cell lymphoma outcome prediction by gene-expression profiling and supervised machined learning" Nature Medicine 8 pp 68-74 (2002) [Ref 8]; and (iii) L. Quijada, M. Soto and J. M. Requena "Genomic DNA microarrays as a tool of gene expression in Leishmania" Expression Parasitology 111, pp 64-70 (2005) [Ref 9].

As for a DNA chip for example, one or several oligonucleotides or polynucleotides may be grafted or absorbed on the organic and/or luminescent organometallic nanocrystals that emerge from the surface of the organic layer and/or organomineral layer of the (nano)material according to the invention. Advantageously, these oligonucleotides or polynucleotides are known specific single strand oligonucleotides or polynucleotides. Their role consists in detecting complementary marked targets which are present in the composite mixture to analysed. As a matter of fact, the detection principle used in the DNA chips relies on the possibilities of matching DNA strands with their complementary bases. These oligonucleotides or polynucleotides are as many probes, which enable to hybridise complementary DNA sequences from a biological sample to be analysed. Advantageously, the luminescent organic or organometallic nanocrystals are fluorescent. Once the chip is hybridized, the detection of the channels is carried out by measuring the corresponding fluorescent signal. The images obtained are digitalised to be processed afterwards by processing algorithms specific to such data and implemented through computer means.

The various embodiment described above for the preparation of the (nano)material and supports for the chips, captors and sensors according to the invention can be applied to the implementation of chips, captors or sensors (e.g. solvents, fluorescent compounds, metallic alcoxides, etc.).

More particularly, one or several types of identical or different probes may be grafted or absorbed on the part of the nanocrystals that emerges from the surface of the inorganic and/or organomineral layer. For this purpose, the various embodiments described previously for the (nano)material of the invention (i.e. probes, connection modes, etc) may apply.

The (nano)material according to the invention may allow to obtain a better sensitivity (detection capacity) and for example to gain up to 2 to 3 degrees of amplitude with respect to the present biochips.

This gain in sensitivity may more particularly result from the combination of two main factors:
each nanocrystal may be composed of a very great number of fluorophores (from $10^4$ to $10^{10}$ fluorophores per nanocrystal according to the diameter thereof), and
the transfer of donor-donor energy between fluorophores, thus the light excitation can explore a large field on an average distance of 8 nm, that is twice the Förster radius, the distance of the transfer of energy between a donor (isolated fluorophore) and an energy acceptor.

Thus, the sensitivity may be improved by a factor of 100 and more with respect to an isolated fluorophore.

This improvement may be observed by measuring the number of moles of quenched fluorophores in an aqueous suspension of nanocrystals per mole of inhibitor of fluorescence. The observed inhibition effect (modification of the fluorescence fading) is much more important in the case of nanocrystals.

More particularly, the fluorescent chips according to the invention may have a capacity of detecting (sensitivity) a target molecule among one hundred fluorescent molecules. This detection capacity or sensitivity is better measured using crystals in a solution where the concentrations are better known. An example of such embodiment is given in the example 4 below.

EXAMPLES

The method of partial dissolution of the surface of the sol-gel layers to make organic nanocrystals emerge according to the invention has been applied to various nanocomposite layers, so as to illustrate the generic aspect of the invention. Picklings were implemented on three different sol-gel layers containing different organic nanocrystals. These are detailed in Examples 1 to 3 below.

Example 1

Rubrene Nanocrystals in Thin Silicated Sol-Gel Layers from Precursor TMOS+TMSE

The microcrystalline rubrene powder (1.8 mg; 0.033 mmoles) was dissolved in a solution containing 4.570 mL of tetrahydrofurane, 0.257 mL of tetramethylsiloxane (TMOS), 0.222 mL of 1,2-bis(trimethoxysilyl)ethane (TMSE) and 0.219 mL of a 0.1 M HCl solution. The molar proportions in the initial mixture are as follows: 2 TMOS+1 TMSE+48 THF+10 $H_2O$+0.005 rubrene. ($H_2O$ refers to the quantity of water introduced together with the 0.1 M HCl solution).

The solution is then stored for several days so as to let the hydrolysis and condensation of alcoxide reactions occur. It should be noted that the sol-gel mixture is extremely stable. Then, this mixture can be stored possibly for several weeks or even several months if it is so desired. However, several days are sufficient for the hydrolysis and condensation of the initial alcoxide to be correctly performed.

A volume of 200 μL of the mixture thus obtained is placed on a microscope glass slide.

The microscope slide is then introduced into a spin-coater of the RC8 GYRSET type manufactured by the Suss Microtech Company. The thin sol-gel layer is obtained by spin-coating under the following conditions:
Rotation speed: 4,000 rpm
Acceleration: 3,000 $rpm^2$
Duration of the rotation: 10 s The thin layer thus obtained is then annealed at 100° C. between 24 hrs and 72 hrs.

Figure 2:
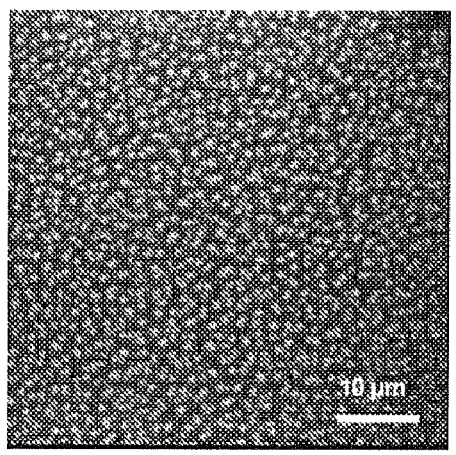
FIG. 2 shows an exemplary picture from a confocal photonic microscopy of rubrene nanocrystals in a sol-gel array from TMOS/TMSE precursor.
Figure 3:
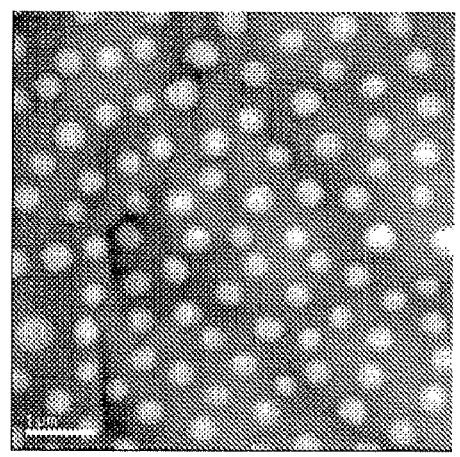
FIG. 3 shows an exemplary image by transmission electronic microscopy of rubrene nanocrystals in a sol-gel array from TMOS/TMSE precursor.

Then, rubrene nanocrystals having an average diameter of 200 nm thus obtained and included in a 250 nm thick thin layer. The nanocrystals have been viewed using a confocal optical microscope (FIG. 2) and a transmission electron microscope (FIG. 3).

The thin layer of nanocomposites inlaid with rubrene nanocrystals is then submitted to controlled dissolution conditions. Thus, the thin layer is pickled to let the rubrene nanocrystals appear on the surface by soaking it into a diluted ($10^{-3}$M) NaOH solution for 16 hrs.

Figure 4:
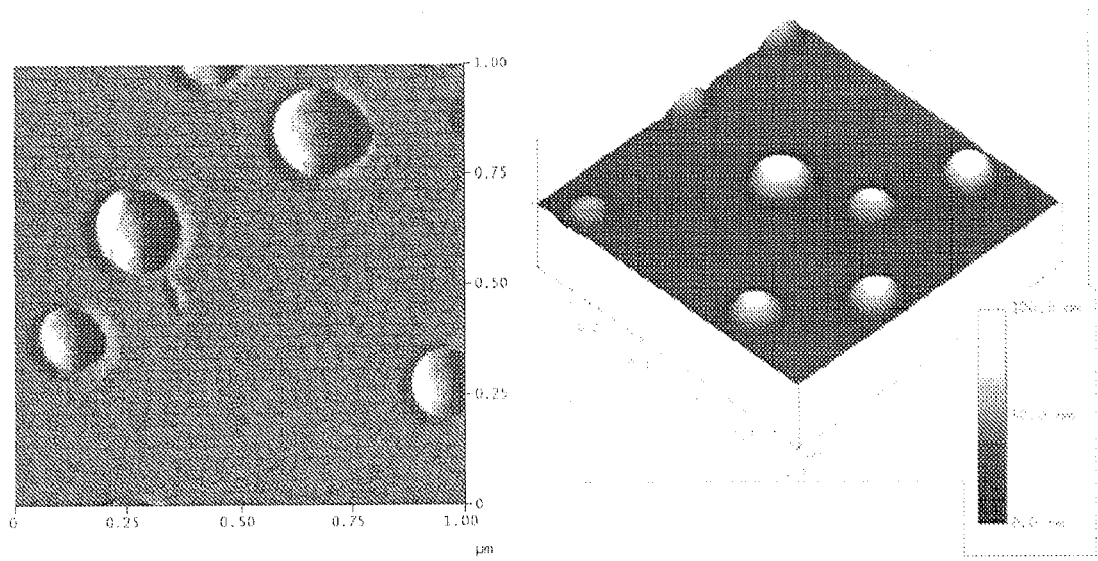
FIG. 4 shows an exemplary image recorded with an atomic force microscope (AFM) in an intermittent mode showing rubrene nanocrystals that emerge by approximately 35 nm from the surface of a thin sol-gel layer from TMOS/TMSE precursor.

Nanocrystals that emerge at the surface of the sol-gel layer are presented in FIG. 4. Such figure makes it possible to directly visualise a slide supporting a sol-gel layer having a very low roughness (0.5 nm RMS) which support nanocrystals that emerge and which are the signalling function of this new type of detector.

The images in FIG. 4 have been recorded with an atomic force microscope (AFM) in an intermittent mode showing the rubrene nanocrystals that emerge from the surface of the thin sol-gel layer. Such images show that the nanocrystals are in contact with the outside environment but that they remain anchored in the layer. They are pickled at less than 50% of their diameter, and of the order of 30% maximum. The nanocrystals emerge by approximately 35 nm above the sol-gel layer. No loss (hole) of nanocrystals can be observed on these pickled layers which are thus ready to be functionalised.

These samples are an exemplary basic embodiment (signalling function of this new type of biochip). Then, we have been able to master the pickling of the surface of our sol-gel layers through a slow dissolution (2-3 nm/hr) thus enabling the organic nanocrystals to emerge while keeping the same roughness of approximately 0.5 nm in RMS at the level of the silicated layer. This preservation of the very low roughness of the sol-gel layer is the perfect illustration of the control of the pickling which is very homogeneous on the thickness of the whole layer according to a molecular single layer dissolution method which is remarkable.

Example 2

Rhodamine B Nanocrystals in Thin Silicated Sol-Gel Layers from TMOS/GPTMS Precursor A sol-gel mixture was prepared according to an operation mode similar to that of Example 1, using 21.7 mg of microcrystalline powder of rhodamine B, 3.662 mL of MeOH, 0.267 mL of tetramethylsiloxane (TMOS), 0.599 mL of 3-glycidoxypropyl)trimethoxysilane (GPTMS) and 0.277 mL of a 0.1 M HCl solution. The molar proportions in the initial mixture are as follows: 0.4 TMOS+0.6 GPTMS+20 MeOH+8 $H_2O$+0.01 rhodamine B. ($H_2O$ refers to the quantity of water introduced in the 0.1 M HCl solution).

The mixture thus obtained is stored for several days so that the hydrolysis and condensation reactions of alcoxides are well advanced. It should be noted that the sol-gel mixture is very stable. Then, the mixture may be left in storage for several weeks or even several months if so desired. However, several days are sufficient for the hydrolysis and the condensation of the starting alcoxides to be properly carried out.

A thin sol-gel layer was placed on a microscope slide by spin-coating in spin coating and annealing conditions similar to those of Example 1.

Thus, rhodamine B nanocrystals having an average diameter of 40 nm are obtained and included in a thin silicated layer, 180 nm in thickness.

The slide is then dipped into a $1.10^{-3}$ mol/L NaOH solution for 4 hrs.

Figure 5:
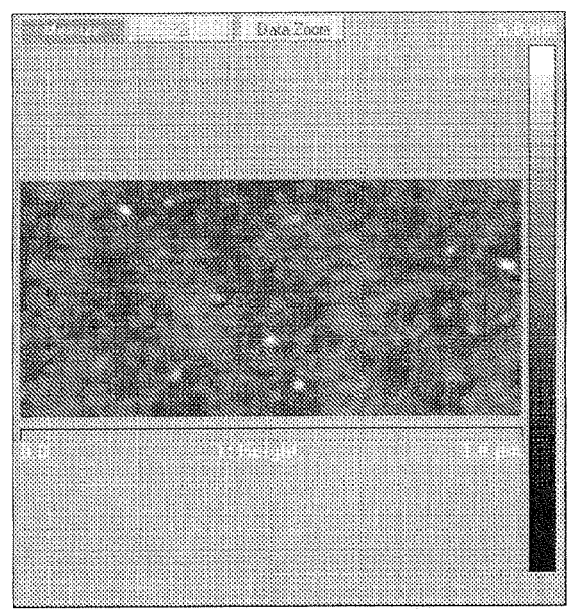
FIG. 5 shows an exemplary image recorded with a near field atomic force microscope (AFM) showing rhodamine B nanocrystals that emerge by 2 to 3 nm from the surface of a thin silicated sol-gel layer from TMOS/GPTMS precursor.

Nanocrystals emerge after pickling of 2 to 3 nm (refer to FIG. 5).

The dissolution speed for this array and the $1.10^{-3}$ mol/L NaOH solution is approximately 2 nm per hour, thus confirming the results from the previous example.

Example 3

Auramine O Nanocrystals in Thin Silicated Sol-Gel Layers from TMOS/TMSE Precursor A sol-gel mixture was prepared according to an operating mode similar to that of Example 1, using 42.36 mg of microcrystalline powder of auramine O, 3.528 mL of THF, 0.257 mL of tetramethylsiloxane (TMOS), 0.222 mL of 1,2-bis(trimethoxysilyl)ethane (TMSE) and 0.219 mL of a 0.1 M HCl solution. The molar proportions in the initial mixture are as follows: 2 TMOS+1 TMSE+75 THF+10 $H_2O$+0.04 auramine O. ($H_2O$ refers to the quantity of water introduced in the 0.1 M HCl solution).

The mixture thus obtained is stored for several days (3 to 4 days), so that the reactions of hydrolysis and condensation of alcoxides are well advanced. It should be noted that the sol-gel mixture is very stable. The mixture can be stored for several weeks or even several months if so desired. However, several days are sufficient for the hydrolysis and condensation of the alcoxides to be correctly executed.

A thin sol-gel layer was produced on a microscope slide by spin-coating under spin-coating and annealing conditions similar to those of the preceding examples.

Thus auramine O nanocrystals having an average diameter of 200 to 300 nm are obtained and included in a thin silicated layer, 300 nm of thickness.

The slide was then dipped into a $1.10^{-1}$ mol/L NaOH solution for 1 h30. It should be noted that the pickling method also works with a more concentrated solution than those used in the preceding examples. The dissolution speed is then increased.

Figure 6:
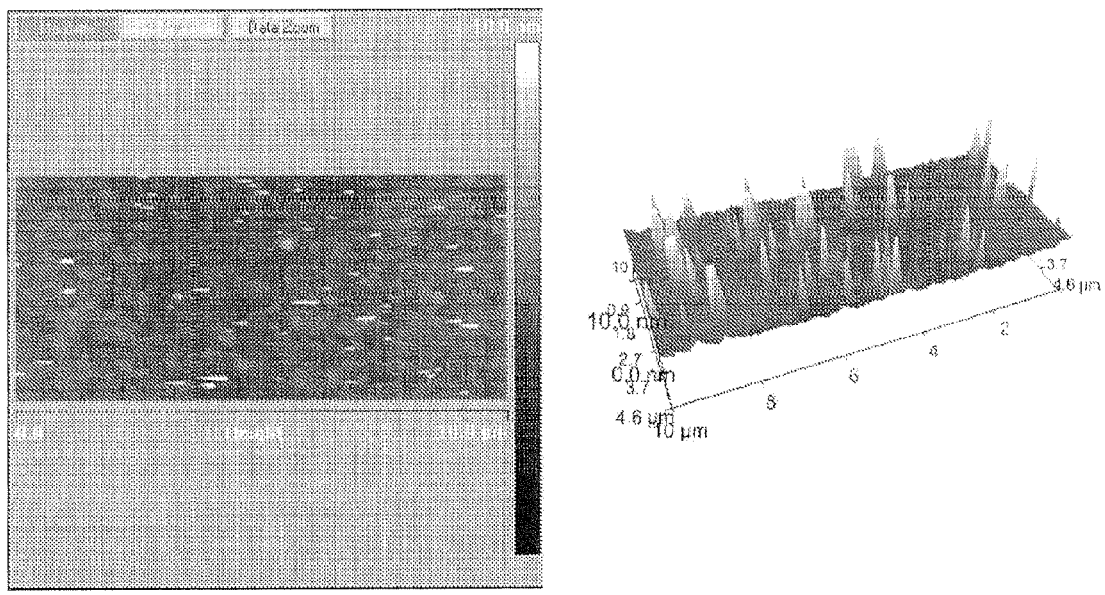
FIG. 6 shows an example of images recorded with a near field atomic force microscope (AFM) showing auramine O nanocrystals that emerge by 15 to 20 nm from the surface of a thin silicated sol-gel layer from precursor TMOS/TMSE.

Upon completion of pickling, nanocrystals emerge by 15 to 20 nm (refer to FIG. 6). The dissolution speed for such an array and for [NaOH]=$1.10^{-1}$ mol/L is approximately 8 to 10 nm per hour.

The three previous examples show the possibility of applying the invention to various sol-gel layers and various types of nanocrystals having various sizes.

Example 4

Figure 1:
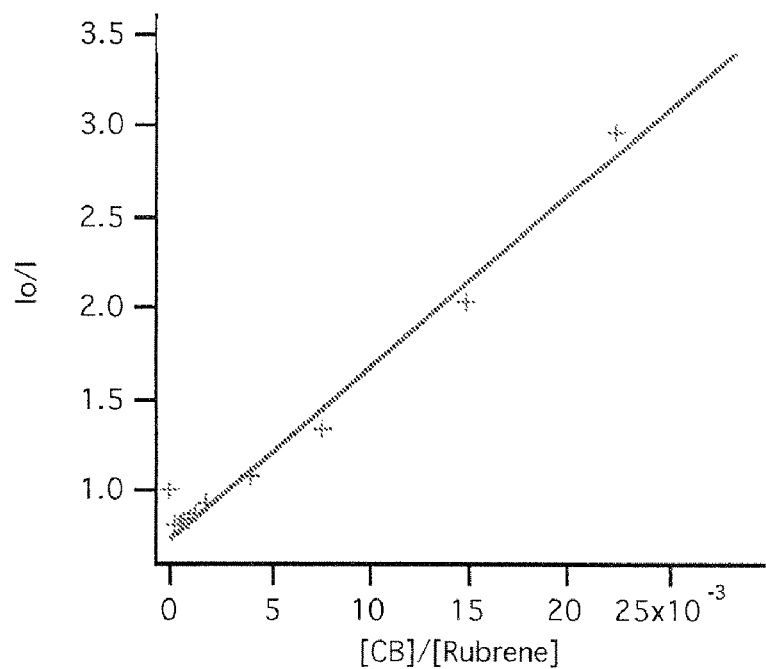
FIG. 1 shows an exemplary "Stern Volmer" Io/I curve, the slope of which gives the number of rubrene molecules in the nanoparticle which are quenched by each quencher molecule, cibacron blue (CB) for example. In other words, this is the average number of rubrene molecules per fluorescent organic nanocrystal which are quenched for each quencher molecule.

An aqueous suspension of nanocrystals is prepared. 10 mL of a 1.3 mmol/L rubrene solution in a mixture of ethanol/THF 3:7 is injected with a syringe having a small needle into 100 mL of a 5 mmol/L aqueous CTACl (cethyl trimethyl ammonium chloride) solution. The solution is filtrated through a Millipore filter with a 50 nm mesh. The concentration in fluorescent molecules is measured by absorption in a quartz bowl having an optical path of 1 cm. The fluorescence is measured in a spectrofluorimeter SPEX Fluorolog with an excitation of 495 nm with 2 nm slots for the emission and the excitation. Its fluorescence intensity was measured for known additions of quencher (probe molecule which inhibits the fluorescence of nanocrystals by non radiating energy transfer between the initially excited nanocrystal and this molecule which is on the surface on the nanocrystal). A typical quencher is cibachron blue. Another one is methylene blue. Both can be dissolved to 1 mmol/L in water. FIG. 1 shows that with one quencher for 100 molecules of rubrene, 33% of quenching of fluorescence is obtained. The Io/I "Stern Volmer" curve is a straight line according to the absorption of the quencher, cibacron blue (CB) on the rubrene nanocrystals in this example. The slope gives the number of rubrene molecules in the nanoparticles, the fluorescence of which is quenched by each quencher molecule.

LIST OF REFERENCES (1) C. J. Brinker and G. W. Scherer, Sol-Gel Science, The Physics and Chemistry of SolGel Processing, Academic Press, New York, 1990.
(2) D. Avnir, V. R. Kaufman and R. Reisfeld, J. Non. Cryst. Solids, 1985, 74, 395-406.
(3) C. Sanchez and F. Ribot, New J, Chem., 1994, 18, 1007-1047.
(4) French patent FR 2 853 307.
(5) WO 2004/042376.
(6) WO 2007/045755.
(7) D. L. Gerhold, "Better Therapeutics through microarrays", Nature Genetics, 32, p 547-552 (2002).
(8) M. A. Shipp "Diffuse large B-cell lymphoma outcome prediction by gene-expression profiling and supervised machine learning" Nature Medicine 8 pp 68-74 (2002).
(9) L. Quijada, M. Soto and J. M. Requena "Genomic DNA microarrays as a tool of gene expression in leishmania" Expression Parasitology, 111, 00 64-70 (2005).

Each one of the above references is integrated therein by reference in totality.

The invention claimed is:

1. A material comprising at least one inorganic and/or organomineral layer integrated into which is at least one type of organic or organometallic fluorescent nanocrystal that emerges from the surface of said layer so that at least one part of the nanocrystal is in direct contact with the outside environment.

2. A material according to claim 1 wherein the inorganic and/or organomineral layer is a sol-gel array of the Silicate, Titanate, Zirconate, Stannate, Borate, Aluminate or Yttriate type.

3. A material according to claim 1 or 2 in the form of a film.

4. A material according to claim 1, wherein said at least one nanocrystal comprises at least one organic molecule or a coordination composite which fluoresces in the solid state and which is soluble in an organic solvent, with the organic molecule or coordination composite selected from fluorescent compounds of the polyaromatic series, the aromatic series, the stilbene series, the naphtilimide series, the rhodamine series, the auramine series, the perylene diimide series, dipyrromethene-boron difluoride derivatives or rare earth composites.

5. A material according to claim 4, wherein the organic molecule or coordination composite is selected from diphenylanthracene, rubrene, tetracene, cyano-methoxy-nitro-stilbene (CMONS), diethyl-amino-nitro-stilbene, naphtilimide, rhodamine B, auramine O or europium composites.

6. A material according to claim 1, wherein said at least one nanocrystal has on the surface thereof at least one type of probe.

7. A material according to claim 6, wherein at least one probe is selected from colored indicators, DNA, the oligonucleotides, polynucleotides, polypeptides, proteins, antibodies, carbohydrates, glycoproteins or lipids.

8. A material according to claim 6 or 7, wherein at least one probe is grafted on said at least one nanocrystal.

9. A material according to claim 1 or 2, wherein said at least one nanocrystal has a diameter ranging from 10 to 500 nm.

10. A material according to claim 1 or 2, wherein said at least one type of nanocrystal has a size distribution varying by +/−20% at most.

11. A material according to claim 1 or 2, wherein said at least one type of nanocrystal emerges by 2 to 50% of the diameter thereof with respect to the inorganic and/or organomineral layer.

12. A film of material characterised in that the material is as defined according to claim 4.

13. A film according to claim 12, positioned on a solid support.

14. A film according to claim 12 or 13 having a thickness ranging from 50 to 1,500 nm.

15. A method for manufacturing the material according to claim 1, said method comprising:
  a) preparing at least one inorganic and/or organomineral layer comprising organic or organometallic fluorescent nanocrystals, and
  b) dissolving a part of said organic or organomineral layer obtained in step a) so as to make at least a part of the nanocrystals of the inorganic and/or organomineral layer emerge therefrom or to increase the surface of the nanocrystals in contact with the outside environment.

16. The method according to claim 15, wherein the step of dissolving is carried out by agents allowing to homogeneously pickle the surface of the inorganic and/or organomineral layer.

17. The method according to claim 16, wherein the agents allowing to pickle are strong or weak basic aqueous solutions.

18. The method according to claim 15, wherein the step of dissolving is controlled to enable a speed ranging from 5 to 100nm/hr for the thinning of the inorganic and/or organomineral layer, by pickling the inorganic and/or organomineral layer.

19. The method according to claim 15, wherein the step of preparing at least one inorganic and/or organomineral layer comprises crystallising organic or organometallic fluorescent nanocrystals in thin layers of a sol-gel array.

20. The method according to claim 19, comprising annealing the sol-gel.

* * * * *